United States Patent [19]

Grandjean

[11] Patent Number: 5,067,960
[45] Date of Patent: Nov. 26, 1991

[54] MUSCLE FITNESS DETECTION BY COLORIMETRY

[75] Inventor: Pierre-Andre Grandjean, Bassenge, Belgium

[73] Assignee: Medtronic, Inc., Minneapolis, Minn.

[21] Appl. No.: 446,593

[22] Filed: Dec. 6, 1989

[51] Int. Cl.⁵ .............................................. A61M 1/10
[52] U.S. Cl. ........................................... 623/3; 600/16
[58] Field of Search .................. 600/16, 17, 18; 623/3

[56] References Cited

U.S. PATENT DOCUMENTS

| | | | |
|---|---|---|---|
| 3,873,267 | 3/1975 | Swartz | 128/632 |
| 4,143,661 | 3/1979 | LaForge et al. | 128/419 R |
| 4,384,829 | 5/1983 | Conley et al. | 623/3 |
| 4,453,537 | 6/1984 | Spitzer | 600/17 |
| 4,457,673 | 7/1984 | Conley et al. | 623/3 |
| 4,666,443 | 5/1987 | Portner | 500/16 |
| 4,685,446 | 8/1987 | Choy | 600/18 |
| 4,771,765 | 9/1988 | Choy et al. | 600/18 |
| 4,813,421 | 3/1989 | Baudino et al. | 128/419 PG |

Primary Examiner—Randy Citein Shay
Attorney, Agent, or Firm—John L. Rooney

[57] ABSTRACT

Apparatus and method for monitoring the performance of skeletal muscle used in a skeletal muscle powered cardiac assist system. The monitoring is performed by an oxygen sensor which determines the adequacy of circulatory support to the skeletal muscle. An adequately supported skeletal msucle can offer the desired cardiac assistance chronically. Insufficient support indicates that the skeletal muscle will easily fatigue until adequate vascularization is achieved. If the circulatory support is chronically insufficient, the risk of ischemia becomes high and additional surgical intervention may be required.

7 Claims, 7 Drawing Sheets

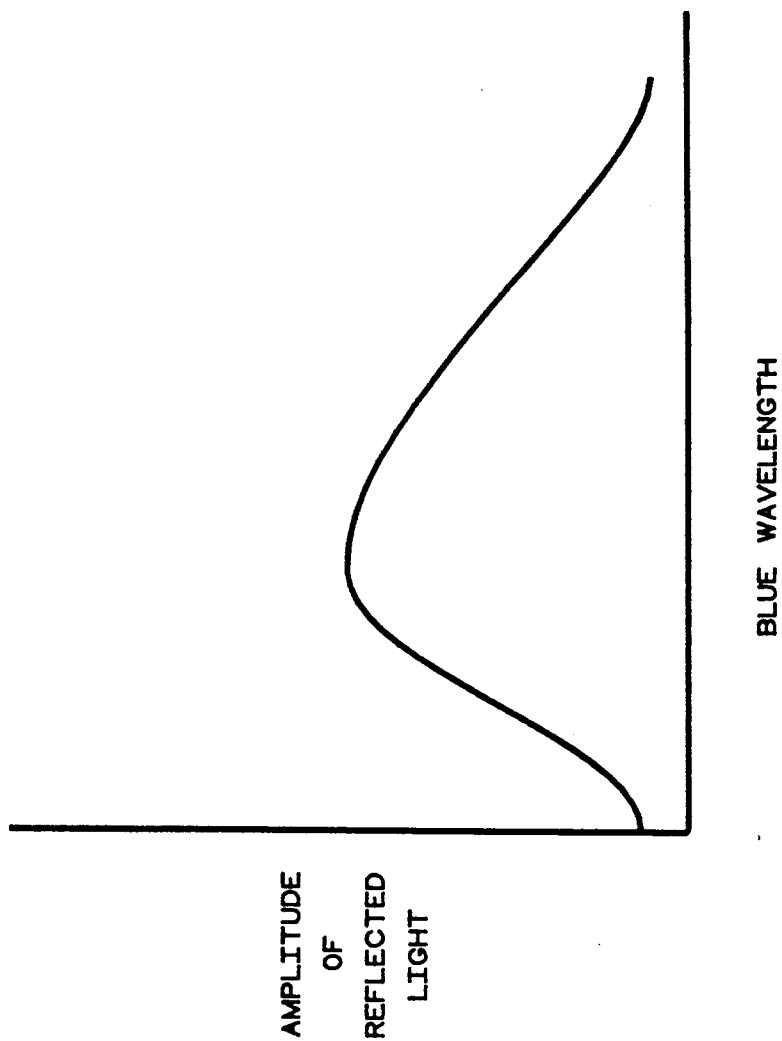

MUSCLE FITNESS DETECTION BY COLORIMETRY

CROSS REFERENCES TO CO-PENDING APPLICATIONS

This application is related to Ser. No. 07/446,594, filed Dec. 6, 1989, pending, entitled "Steroid Eluting Intramuscular Lead" by the same assignee; Ser. No. 07/446,592, filed Dec. 6, 1989, pending, entitled "Muscle Output Monitor by Intramuscular Temperature Variation Measurement" by the same assignee; and Ser. No. 07/446,811, filed Dec. 6, 1989, pending, entitled "Muscle Contraction Control by Intramuscular Pressure Monitoring" by the same assignee.

BACKGROUND OF THE INVENTION

1. Field of the Invention

The present invention relates generally to cardiac assist systems, and more particularly, relates to monitoring of cardiac assist systems which are powered by skeletal muscle.

2. Description of the Prior Art

Cardiac assist systems do not replace the human heart, but merely supplement it. Many techniques have been proposed using a variety of mechanical power sources. Typically these required some form of percutaneous energy transfer because of the difficulty in storing sufficient energy subcutaneously. Such systems are cumbersome and inconvenient for the patient, and are prone to infection along the percutaneous energy transfer path.

A technique holding a great deal of promise is to power the cardiac assist system from a surgically modified skeletal muscle. The cardiac assist system is thus powered by normal biochemical processes. U.S. Pat. No. 4,813,952 issued to Khalafalla teaches a number of configurations of a skeletal muscle powered cardiac assist system.

One problem peculiar to a skeletal muscle powered cardiac assist system is that the skeletal muscle must be conditioned to the constant load of continuous contraction/relaxation demanded of the myocardium. U.S. Pat. No. 4,411,268 issued to Cox teaches a technique for conditioning the skeletal muscle. Whereas the apparatus of Cox is effective to accomplish this conditioning, his system has no provisions for chronically monitoring the stability of the skeletal muscle following the conditioning process. In practice this necessitates the attention of highly skilled medical personnel to monitor the operation of the skeletal muscle with sophisticated instrumentation and to exercise manual control of the stimulation regimen with pulse generator programming equipment. Furthermore, neither Cox nor Khalafalla teach a real time monitoring mechanism, whereby adequate vascular support to the skeletal muscle can be chronically verified.

SUMMARY OF THE INVENTION

The preferred mode of the present invention employs a chronically implantable oximeter which is positioned within the skeletal muscle of a cardiac assist system. It is preferably a two wave length reflectance oximeter which measures the relative oxygen level within the skeletal muscle as it powers the cardiac assist system. The two wavelength reflectance signal is sent to be processed within the implantable pulse generator of the cardiac assist system.

Circuitry which is internal to the implantable pulse generator determines the relative oxygen level and performs a trend analysis concerning the chronic sufficiency of the vascularization of and circulatory support to the skeletal muscle. This data is stored in memory within the implantable pulse generator. This memory may be interrogated by medical personnel using telentry to obtain status and trend information concerning the cardiac assist system.

The data may be analyzed by medical personnel to determine the effectiveness of conditioning, the sufficiency of maintenance stimulation, the adequacy of vascularization, and the chronic prognosis for the cardiac assist system. This enables the medical personnel to manually modify the conditioning regimen, change the maintenance stimulation, institute various drug therapies, and plan for necessary surgical intervention.

BRIEF DESCRIPTION OF THE DRAWINGS

Other objects of the present invention and many of the attendant advantages of the present invention will be readily appreciated as the same become better understood by reference to the following detailed description when considered in connection with the accompanying drawings, in which like reference numerals designate like parts throughout the figures thereof and wherein:

FIG. 7 is a graphical representation of the oximetry return in an oxygen insufficient environment.

DETAILED DESCRIPTION OF THE PREFERRED EMBODIMENTS

The present invention employs a sensor implanted within the skeletal muscle of a skeletal muscle-powered cardiac assist system to chronically monitor the adequacy of circulatory support. The cardiac assist system may be configured in a variety of ways as described in U.S. Pat. No. 4,813,952 issued to Khalafalla, herein incorporated by reference. Several of these configurations are discussed herein by way of illustration and are not intended to limit the present invention.

Figure 1:
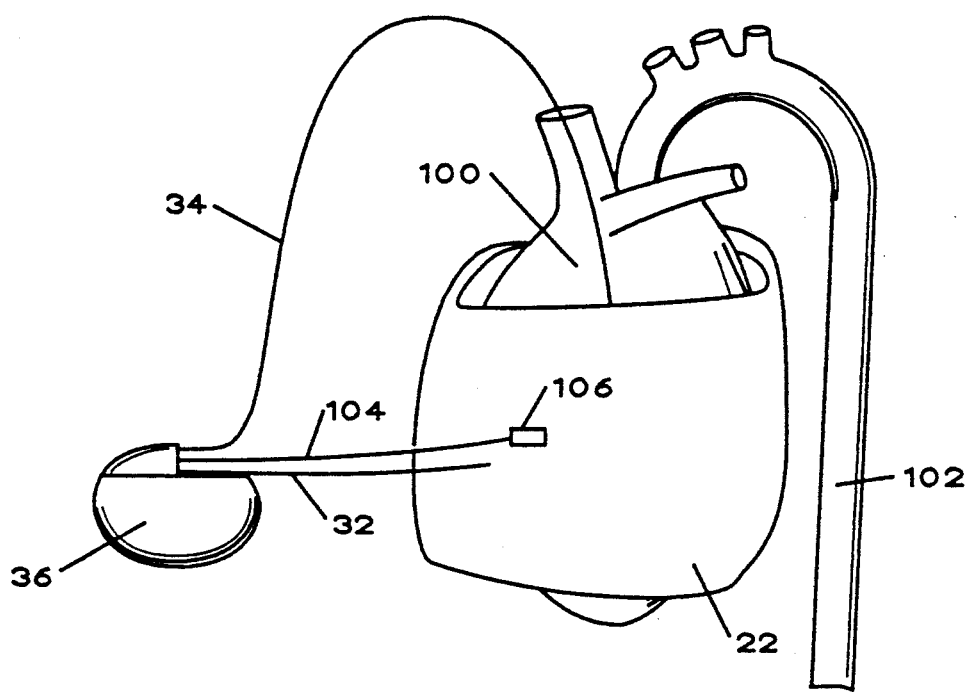
FIG. 1 is a first embodiment of the present invention wherein the skeletal muscle is wrapped about the myocardium.

FIG. 1 is an embodiment of the present invention wherein skeletal muscle 22 is wrapped about human heart 100. Skeletal muscle 22 is conditioned as a "slow twitch" muscle as described by Cox in U.S. Pat. No. 4,411,268, herein incorporated by reference. Implantable pulse generator 36 is coupled to pacing lead 34 to produce a demand pacemaker as taught by Cox. In addition, implantable pulse generator 36 stimulates skeletal muscle 22 to contract in synchrony with human heart 100. Assistance to human heart 100 is provided by the simultaneous contraction of skeletal muscle 22 to increase systolic pressure in descending aorta 102 and elsewhere in the circulatory system.

According to the present invention, a sensor 106 is implanted within skeletal muscle 22 to determine the adequacy of vascular support. The data measured by sensor 106 is transferred to implantable pulse generator 36 via lead 104 where it is processed, stored and telemetered percutaneously using normal implantable pulse generator telemetry circuitry for analysis by medical personnel.

Figure 2:
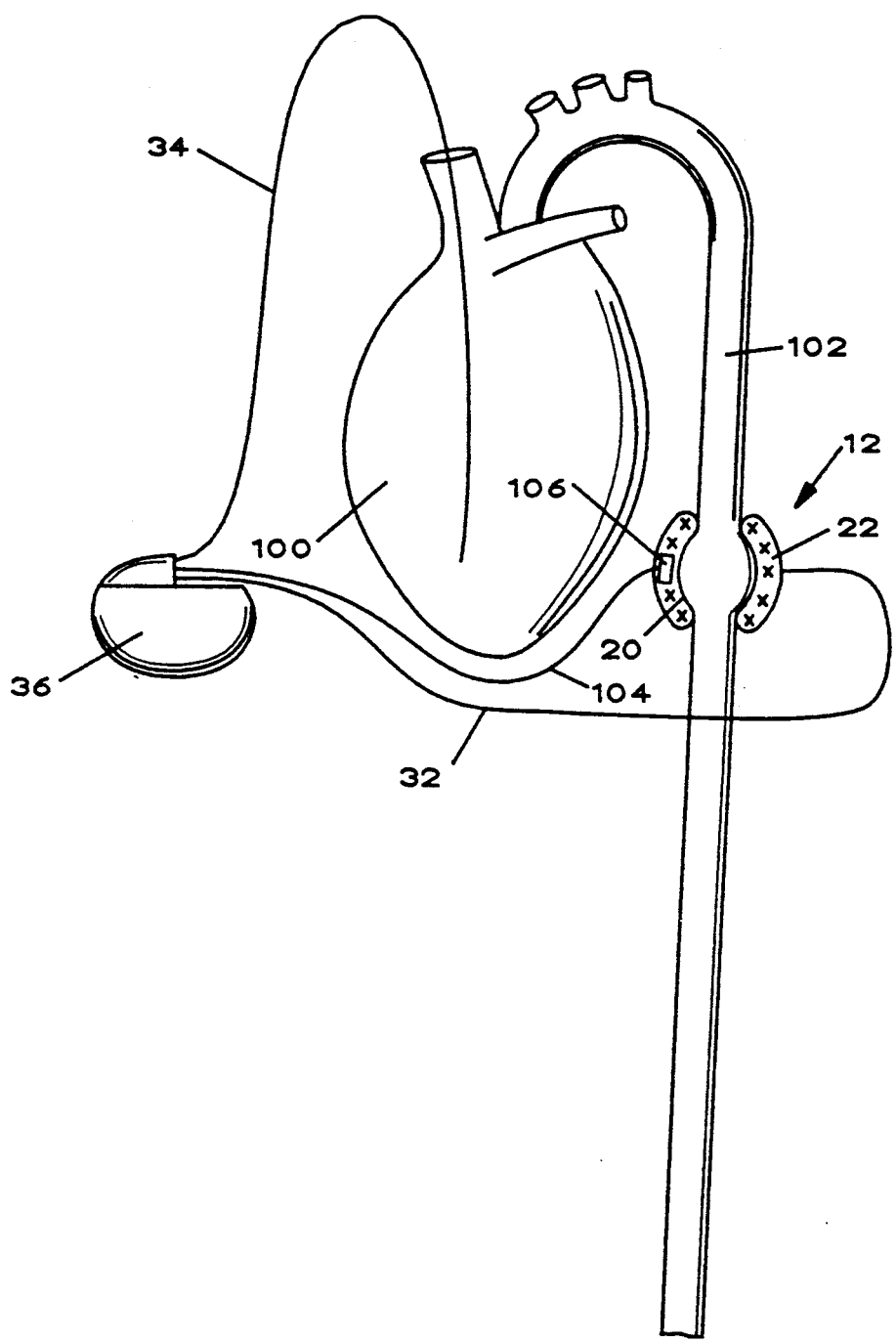
FIG. 2 is an alternative embodiment of the present invention wherein the skeletal muscle is wrapped about the descending aorta.

FIG. 2 is an alternative embodiment of the present invention. In this embodiment skeletal muscle 22 is wrapped about artificial chamber 20 inserted in series with descending aorta 102. Unlike the embodiment of FIG. 1, implantable pulse generator 36 stimulates skeletal muscle 22 to contract following evacuation of human heart 100. This is accomplished by the insertion of a delay between a paced or sensed beat of human heart 100 and the stimulation of skeletal muscle 22.

Figure 3:
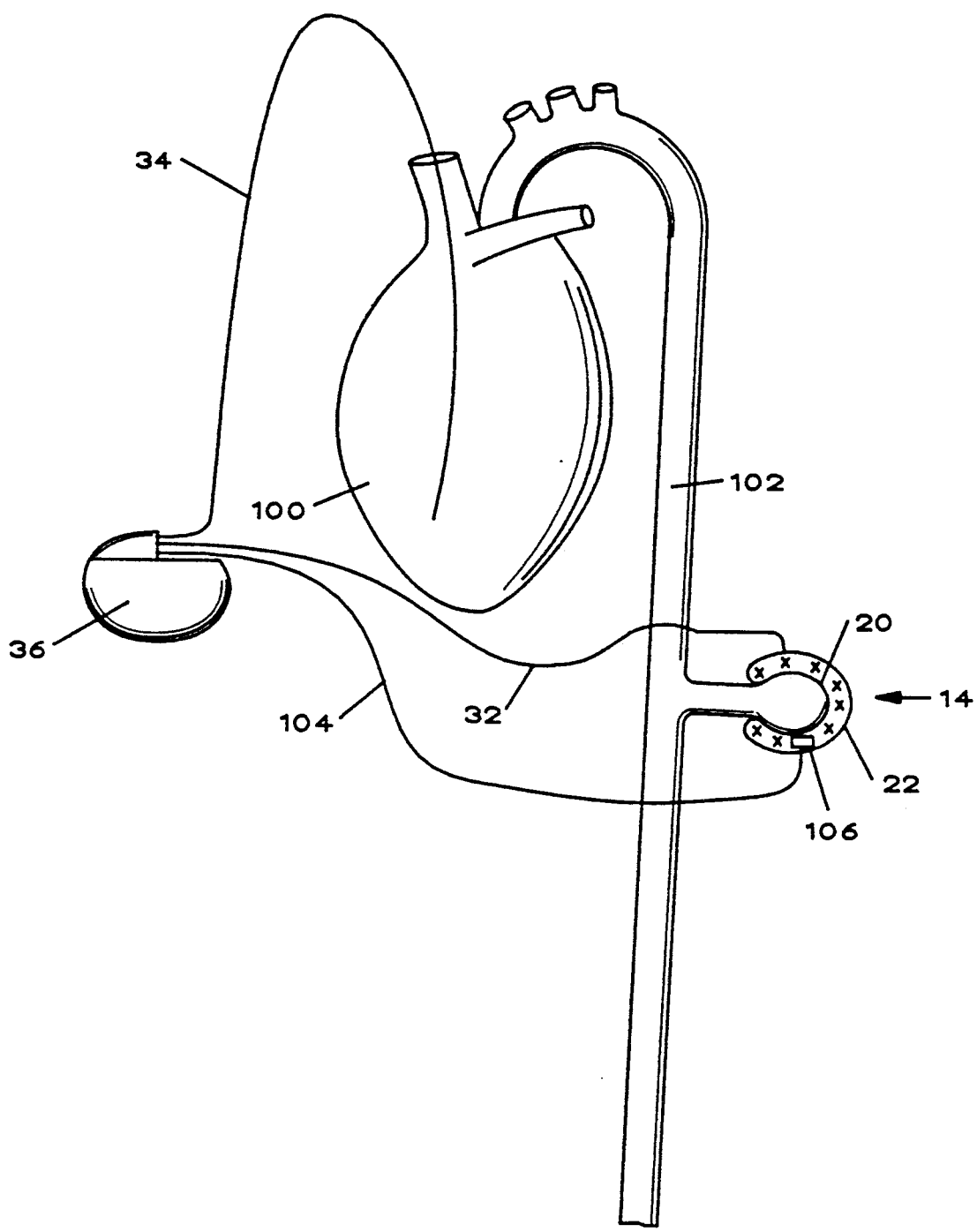
FIG. 3 is an alternative embodiment of the present invention wherein the skeletal muscle performs counter pulsation of the descending aorta.

FIG. 3 is a further embodiment wherein artificial chamber 20 is coupled external to descending aorta 102. In this configuration skeletal muscle 22 is stimulated to counter pulse human heart 100. This raises diastolic pressure, thereby increasing perfusion of human heart 100. This is accomplished by the insertion by implantable pulse generator 36 of a sufficient delay between a sensed or paced contraction of human heart 100 and stimulation of skeletal muscle 22 to cause the desired counter pulsation.

Figure 4:
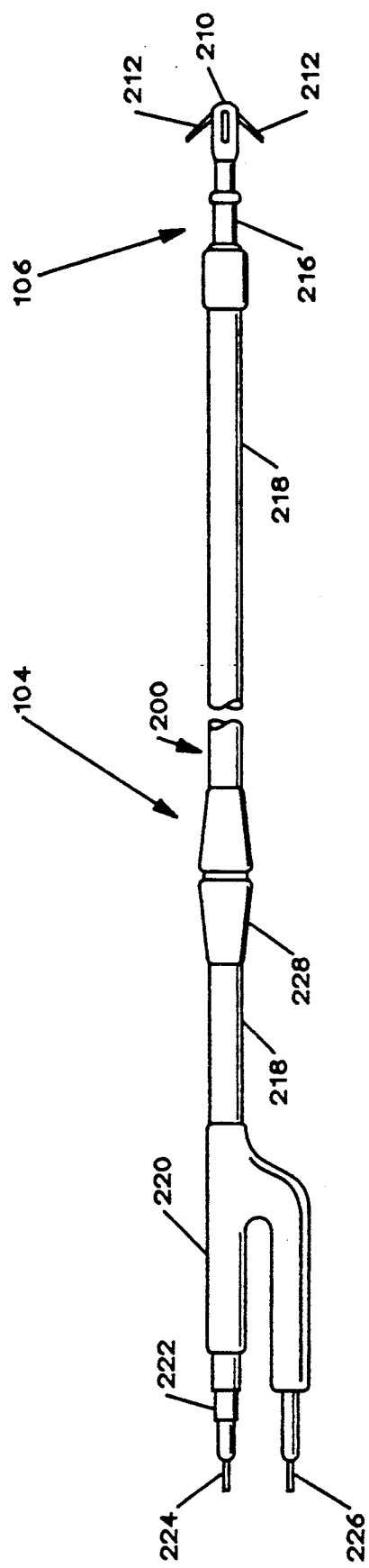
FIG. 4 is a plan view of the oximetry probe.

FIG. 4 is a plan view of lead 104 coupled to sensor 106. U.S. Pat. No. 4,813,421 issued to Baudino, et al., herein incorporated by reference, describes the preferred embodiment of sensor 106 and lead 104 in greater detail.

Lead 104 is a typical chronically implantable lead. It contains an insulated, bifurcated proximal connector assembly 220 which sealingly plugs into implantable pulse generator 36. The proximal end of connector assembly 220 contains terminal pins 224 and 226. A third conductor within lead 104 is terminated at ring terminal 222. The main body of lead 104 is covered with biocompatible outer sheath 218 of silicone rubber or polyurethane. Anchoring sleeve 228 facilitates securing of the proximal end of lead 104 in the manner well-known in the art.

The distal end 210 of lead 104 contains sensor 106 which is preferably a two wavelength reflectance oximeter as taught by Baudino, et al. Maintenance of the position of sensor 106 may be facilitated by tine members 212 which work particularly well for positioning of transveneous pacing leads as is well-known in the art. Oximetry structure 216 is positioned near distal end 210. Oximetry structure 216 is covered with synthetic sapphire as taught by Baudino, et al.

Figure 5:
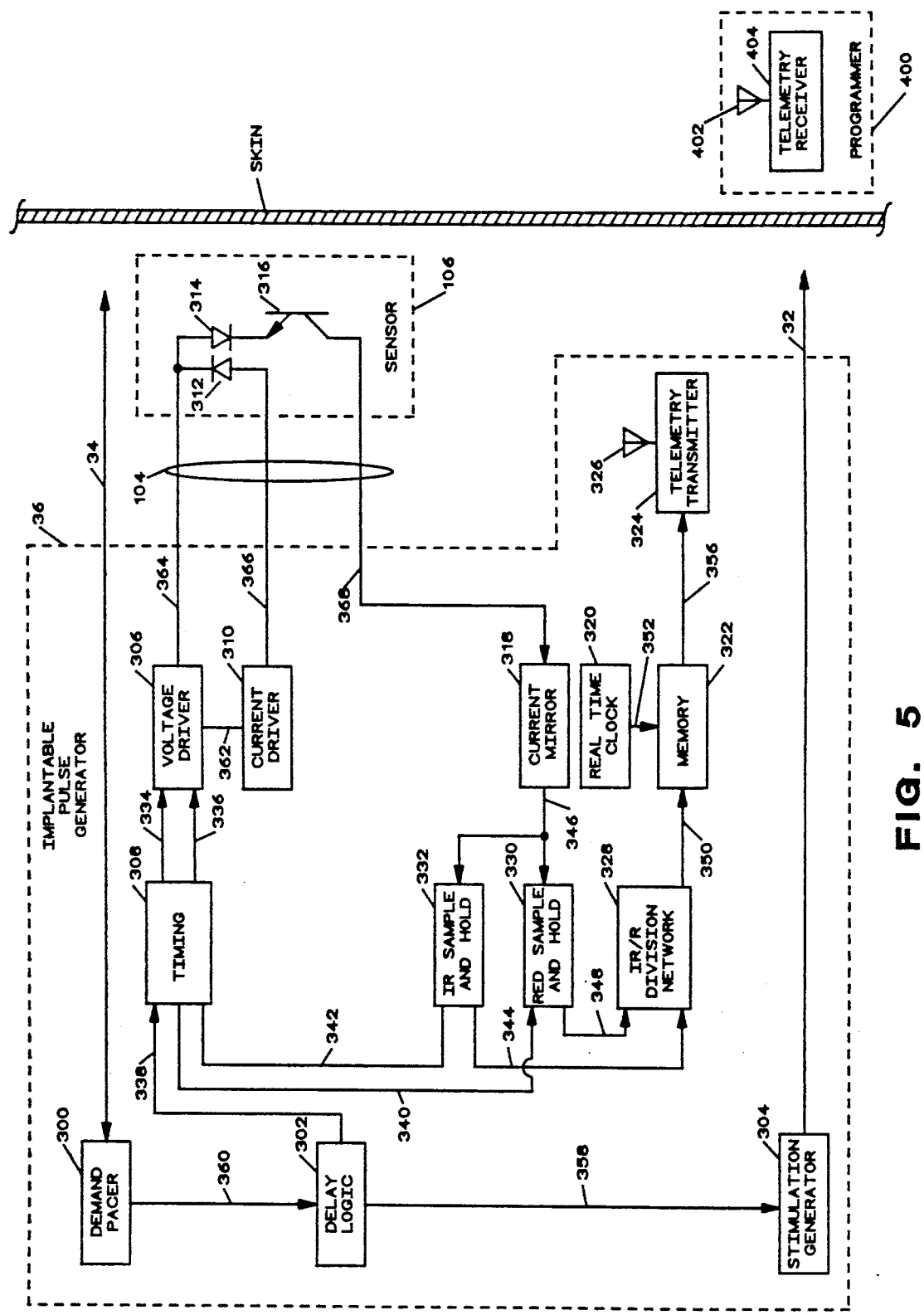
FIG. 5 is a block diagram of the implantable pulse generator.

FIG. 5 is an overall block diagram of the circuitry within implantable pulse generator 36. Demand pacer 300 is constructed according to circuitry known in the art of pacing and communicates with human heart 100 via lead 34. Demand pacer 300 notifies delay logic 302 via line 360 of a contraction of human heart 100. This may be the result of either a sensed natural heart contract or an artificially generated pacing pulse. In either situation, delay logic 302 generates a delay appropriate to the particular embodiment (see above) and signals stimulation generator 304 by line 358 to stimulate skeletal muscle 22 via lead 32. Stimulation generator 304 may also contain muscle conditioning circuitry, which is not shown for clarity. U.S. Pat. No. 4,411,268 issued to Cox should be consulted for a more detailed description of skeletal muscle conditioning. Delay logic 302 also provides timing 308 with a begin sensing signal via line 338. This begin sensing signal is synchronous with the contraction of human heart 100 and delayed from it so that motion artifacts are minimized during the sensing process.

Timing 308 notifies voltage driver 306 via lines 334 and 336 when to energize infrared LED 312 and red LED 314, respectively. Current driver 310, coupled via common line 362 to voltage driver 306, maintains the illumination of each LED to enable photosensor 316 to measure the reflected return. Infrared LED 312, red LED 314, and photosensor 316 are all located within sensor 106 and coupled to implantable pulse generator 36 by lead 104 as shown. Lines 364, 366 and 368 comprise the three conductors of lead 104 (see also FIG. 4).

The sensed return of photosensor 316 is transferred to current mirror 318 via line 368 for processing. After processing, the resultant is transferred to IR sample and hold 332 and red sample and hold 330 by line 346. The signal is gated to the proper sample and hold circuit by timing 308 using gating signals on lines 340 and 342.

IR/R division network 328 compares the infrared and red signals received via lines 344 and 348 to sense color shifts. The periodic sensor outputs of IR/R division network 328 are sent by line 350 to memory 322 for storage awaiting readout by medical personnel. Each measured signal is time tagged by the output of real time clock 320 on line 352.

Medical personnel can access the time-tagged sensor data stored in memory 322 by telemetry techniques common in the implantable device field. Preferably this access is via a radio frequency signal prepared by telemetry transmitter 324 as modulated with data received on line 356 from memory 322. This radio frequency signal is transmitted by radio frequency antenna 326. The signal is received outside of the body by antenna 402, demodulated by telemetry receiver 404 and processed and presented to medical personnel by programmer 400 in the manner known in the art.

An alternative implementation of implantable pulse generator 36 is through the use of a microprocessor controlled general purpose implantable pulse generator such as PROSMETHEUS ™ pulse generator manufactured by Medtronic, B.V. of the Netherlands. The primary advantage of such an implementation is the ease with which such a programmable device can change modes of operation. This is particularly useful when doing clinical research. A description of the use of such a device may be found in the paper "Pulse Generator for Biomechanical Cardiac Assistance by Counter-Pulsation Technique", by Grandjean, et al., published in the "Record of the Conference on Skeletal Muscle for Cardiac Assist and Repair, Bannf Sept. 28–Oct. 2, 1988", published by Futura Editions (August 1989).

Figure 6:
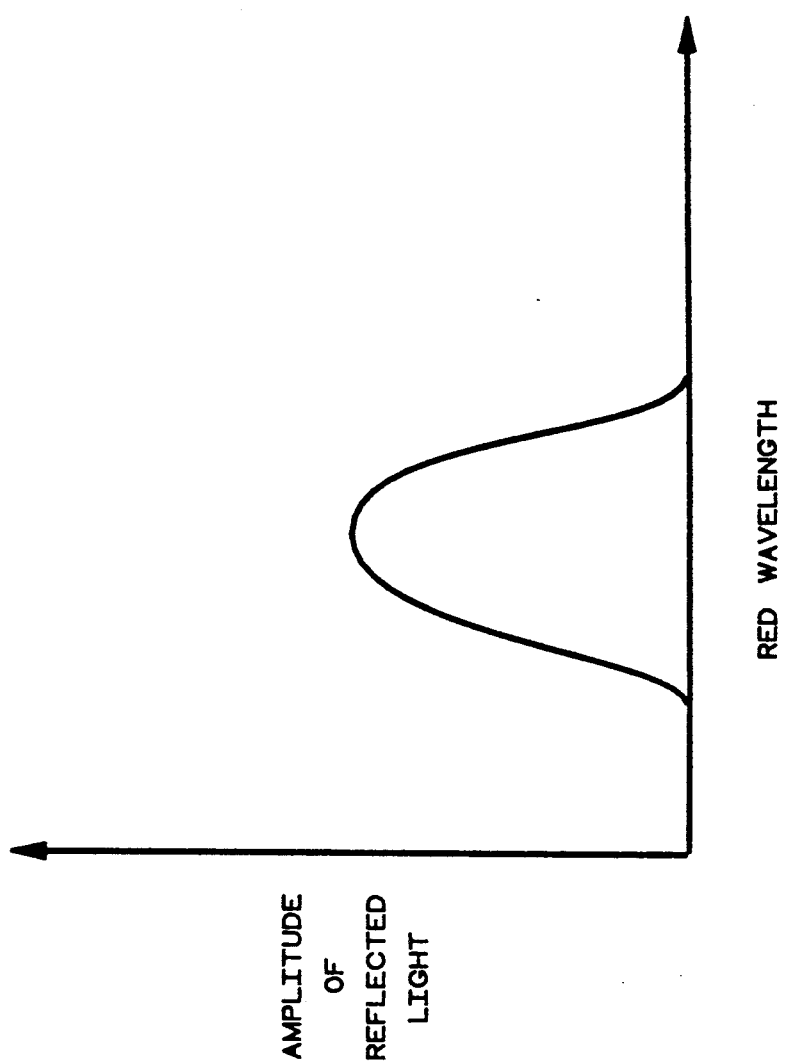
FIG. 6 is a graphical representation of the oximetry return in an oxygen sufficient environment.

FIG. 6 is a graphical representation of the sensed signals from a skeletal muscle 22 which is adequately supported by the vascular system. The amplitude of the reflected light is relatively sharply peaked within the region of visible red wavelengths. This indication when read from memory 322 via telemetry indicates that skeletal muscle 22 was receiving sufficient support for its workload at the time tag of the sensor reading. A complete series of such signals stored within memory 322 verifies that skeletal muscle 22 continues to be healthy.

FIG. 7 shows the response of sensor 106 when skeletal muscle 22 is not adequately supported by the vascular system. As can be seen, the amplitude of reflected light is shifted to the blue wavelengths and is not sharply defined. Medical personnel upon seeing this indication from memory 322 will conclude that skeletal muscle 22 is not receiving sufficient oxygen for its workload. Continuation of this state indicates a high risk of ischemia to a portion or all of skeletal muscle 22.

Immediate medical action includes reduction of the physical load on skeletal muscle 22 by reducing the duty cycle of stimulation pulses. Total cessation of stimulating pulses will place skeletal muscle 22 at rest without any load. Skeletal muscle 22 may respond to additional conditioning as taught by Cox. In severe cases, surgical intervention may be required.

Having thus described the preferred embodiments of the present invention, those of skill in the art will be able to readily apply these teachings to other embodiments without deviating from the scope of the claims hereto attached.

I claim:

1. A cardiac assist system for assisting a natural human heart having ventricles which contract at a ventricular rate comprising:
   a. a surgically prepared skeletal muscle adapted to be responsively coupled to the circulatory system;
   b. control means adapted to be coupled to said natural human heart and coupled to said surgically prepared skeletal muscle for stimulating said surgically prepared skeletal muscle to contract in synchrony with said ventricles of said natural human heart; and
   c. means responsively coupled to said surgically prepared skeletal muscle for monitoring a parameter indicative of changes in the oxygen level in said surgically prepared skeletal muscle.

2. A cardiac assist system according to claim 1 wherein said monitoring means comprises:
   a. means for sensing changes in the level of oxygen in said surgically prepared skeletal muscle; and,
   b. means responsively coupled to said sensing means for storing data from said sensing means until manually requested.

3. A cardiac assist system according to claim 2 wherein said sensing means is an oximeter.

4. A cardiac assist system according to claim 3 wherein said oximeter is a two wavelength reflectance oximeter.

5. A method of assisting a natural human heart having ventricles which contract at a ventricular rate to produce cardiac circulation comprising the steps of:
   a. surgically coupling a skeletal muscle to the circulatory system;
   b. stimulating said skeletal muscle to contract in synchrony with said ventricles of said natural human heart; and,
   c. chronically monitoring a parameter indicative of changes in the level of oxygen in said skeletal muscle.

6. A method according to claim 5 further comprising storing the data produced by said sensing step.

7. A method according to claim 6 further comprising telemetering out the data from said storing step.

* * * * *